United States Patent
Zinn et al.

(10) Patent No.: US 9,052,025 B2
(45) Date of Patent: Jun. 9, 2015

(54) BIDIRECTIONAL DUCKBILL VALVE APPARATUS AND A METHOD FOR ITS USE

(71) Applicants: Kenneth M. Zinn, Westport, CT (US); Mark Steven Fisher, Sellersville, PA (US)

(72) Inventors: Kenneth M. Zinn, Westport, CT (US); Mark Steven Fisher, Sellersville, PA (US)

( * ) Notice: Subject to any disclaimer, the term of this patent is extended or adjusted under 35 U.S.C. 154(b) by 146 days.

(21) Appl. No.: 13/726,431

(22) Filed: Dec. 24, 2012

(65) Prior Publication Data

US 2013/0160866 A1    Jun. 27, 2013

Related U.S. Application Data

(60) Provisional application No. 61/580,029, filed on Dec. 23, 2011.

(51) Int. Cl.
| | | |
|---|---|---|
| *F16K 17/18* | (2006.01) | |
| *F16K 15/14* | (2006.01) | |
| *A61M 39/24* | (2006.01) | |

(52) U.S. Cl.
CPC .............. *F16K 17/18* (2013.01); *F16K 15/147* (2013.01); *A61M 2039/2493* (2013.01); *F16K 15/145* (2013.01); *A61M 39/24* (2013.01); *A61M 2039/242* (2013.01); *A61M 2039/2426* (2013.01)

(58) Field of Classification Search
CPC .............. A61M 2039/242; A61M 2039/2426; A61M 2039/2493; F16K 17/18; F16K 15/141; F16K 15/16; F16K 15/144; F16K 15/147
USPC .............. 137/493, 493.8, 512.15, 512.4, 846
See application file for complete search history.

(56) References Cited

U.S. PATENT DOCUMENTS

| | | | | | |
|---|---|---|---|---|---|
| 424,632 | A | * | 4/1890 | Ware | 604/299 |
| 703,101 | A | * | 6/1902 | Ware | 604/299 |
| 3,159,176 | A | * | 12/1964 | Russell et al. | 137/493.1 |
| 3,941,149 | A | * | 3/1976 | Mittleman | 137/493.1 |
| 4,181,145 | A | * | 1/1980 | Mitchell | 137/493.8 |
| 5,156,600 | A | | 10/1992 | Young | |
| 6,089,260 | A | | 7/2000 | Jaworski et al. | |
| 6,234,196 | B1 | * | 5/2001 | Fischer et al. | 137/493.8 |
| 6,305,413 | B1 | * | 10/2001 | Fischer et al. | 137/493.8 |
| 7,722,278 | B2 | | 5/2010 | Black | |

* cited by examiner

*Primary Examiner* — Craig Schneider
*Assistant Examiner* — R. K. Arundale
(74) *Attorney, Agent, or Firm* — Muskin & Farmer LLC

(57) ABSTRACT

A bidirectional side-slit duckbill valve apparatus for use with catheters and similar devices. The apparatus can comprise a duckbill valve configured to allow fluid to flow through it only in a first direction and one or more side-slit valves configured to allow fluid to only flow through them in a second direction, opposite the first direction. In an embodiment, fluid can only flow through the duckbill valve if it is under a substantially positive pressure and can only flow through the side-slit valves if it is under a substantially negative pressure. In an embodiment, fluid that is not pressurized will not flow through either the duckbill valve or the side-slit valve. In an embodiment, the bidirectional side-slit duckbill valve apparatus can also comprise a funnel for directing a guidewire.

15 Claims, 10 Drawing Sheets

NEUTRAL

INJECTION

ASPIRATION

BIDIRECTIONAL DUCKBILL VALVE APPARATUS AND A METHOD FOR ITS USE

CROSS REFERENCE TO RELATED APPLICATIONS

This application claims benefit to provisional patent application No. 61/580,029 filed Dec. 23, 2011, which is incorporated by reference herein in its entirety.

FIELD OF THE INVENTION

The present general inventive concept is directed toward a bidirectional valve apparatus configured for use in various catheters and other similar devices.

BACKGROUND

Peripherally inserted central catheters (PICCs), sheaths and port catheters require frequent flushing with heparin and saline to maintain patency due to the open-ended nature of most of these devices. The addition of a bidirectional valve to these devices would eliminate the need for such frequent flushing after an initial post-usage flush is performed because it would prevent blood or other fluid from being pulled into the catheter by a negative pressure existing within the catheter. Currently, this blood must be periodically flushed out of the catheter to prevent the catheter from becoming clogged.

What is needed is a bidirectional valve for use with PICCs, sheaths and other catheters, which can permit the flow of fluids in two opposing directions while being able to provide a sealed environment within these devices when fluid is not flowing in either of these directions.

SUMMARY OF THE INVENTION

It is an aspect of the present device to provide an improved bidirectional valve for use with PICCs, sheaths and catheters and other related devices.

The above aspect can be obtained by a bidirectional side-slit duckbill valve apparatus, comprising: an inverted V-shaped lower section further comprising a first side section having a first end and a second end and a second side section having a first end and a second end, wherein the first side section is connected to a first shoulder at its first end and a trough at its second end and the second side section is connected to a second shoulder at its first end and a trough at its second end; the trough further comprises a duckbill valve opening; and the first shoulder further comprises a first side-slit valve and the second shoulder further comprises a second side-slit valve.

The above aspect can also be obtained by a bidirectional side-slit duckbill valve apparatus, comprising: a V-shaped upper section, further comprising a first side section having a first end and a second end and a second side section having a first end and a second end, wherein the first side section is connected to a first shoulder at its first end and a trough at its second end and the second side section is connected to a second shoulder at its first end and a trough at its second end; the trough further comprises a duckbill valve opening; the first shoulder further comprises a first side-slit valve and the second shoulder further comprises a second side-slit valve; and an inverted V-shaped lower section, further comprising a funnel configured to direct a guidewire through the duckbill valve opening.

This together with other aspects and advantages, which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which.

DESCRIPTION OF THE PREFERRED EMBODIMENTS

Figure 1:
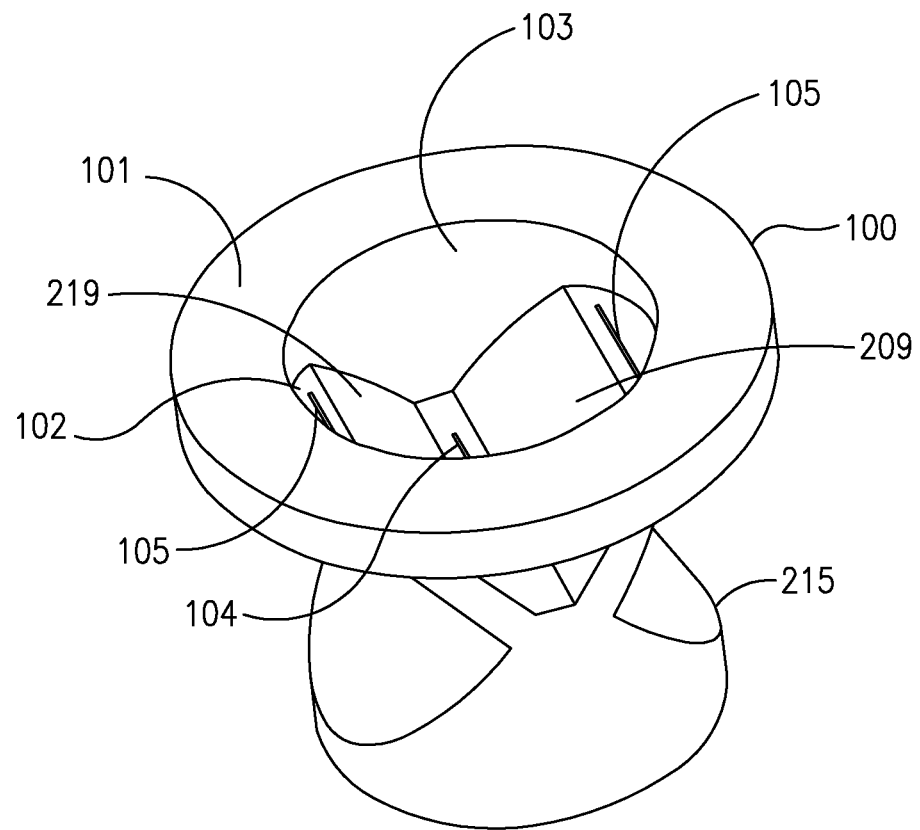
FIG. 1 is a perspective view drawing of the top and side of a bidirectional, side-slit duckbill valve apparatus configured for use with a guidewire (not shown in FIG. 1), according to an embodiment.

Reference will now be made in detail to the presently preferred embodiments of the present device, examples of which are illustrated in the accompanying drawings, wherein like reference numerals refer to like elements throughout.

Peripherally inserted central catheters (PICCs) and port catheters can require routine flushing with heparin and saline to maintain patency during their use. The present valve device can allow such catheters to remain sealed while not in use, thereby eliminating the need for catheter flushing, by preventing blood or other liquid from being pulled up into the catheter by negative pressure existing within the catheter. Furthermore, the present device can comprise a bidirectional valve apparatus, which can allow fluids to flow through the apparatus in two opposing directions by the use of two or more valves that can be opened and closed by the application of negative or positive pressure to the bidirectional valve apparatus. Specifically, the present inventive concept relates to a bidirectional valve apparatus that can comprise a first check valve for controlling the flow of a liquid in a first direction and additional check valves which can control the flow of a liquid in a second direction, opposite the first direction.

The present bidirectional valve apparatus can comprise a duckbill valve for controlling the flow of fluid in the first direction. Duckbill valves allow fluid to flow in only one direction and are commonly used as check valves due to their durability and simplicity. Such valves typically comprise two side sections placed in close proximity to each other, thereby forming a V-shape.

More specifically, a first side section can have a first end and a second end and a second side section can have a first end and a second end. To form the V-shape, the first ends of each side section can be placed into contact with each other to form a trough and to form a first angle between the first side section and the second side section. The second ends of each side section can be located at a first distance from each other. These second ends can each be mounted to a shoulder wherein the trough and the side sections can be suspended from these shoulders. A duckbill valve typically comprises an opening, hereinafter the "duckbill valve opening," located at the trough, where the first ends of each side section meet at the first angle. In the most common configuration, when subjected to neither a positive pressure nor a negative pressure, the duckbill valve can remain in a neutral position wherein the first opening of the duckbill valve can be in a closed position.

Fluid can move through the duckbill valve by passing between the first distance between the second ends of the side sections and then through the opening of the trough located between the first ends of the side sections. When positive pressure is applied to fluid located between the first ends of the side sections and to the duckbill valve generally, these ends can be moved apart and the duckbill valve opening can be enlarged by the fluid creating a second distance between the first ends of the side sections, thus allowing the fluid to pass through the duckbill valve.

When a duckbill valve is used in conjunction with a catheter apparatus, the valve can be used to allow the injection of liquid drug solutions, intravenous fluids, blood or other liquids into the body when such liquids are subjected to a substantially positive pressure and moved in a first direction through the first ends of the side sections comprising the duckbill valve, while preventing blood from flowing out of the patient's body, in a second direction, opposite the first direction, when this positive pressure is not present. When subjected to a substantially negative pressure, the duckbill valve can actually close more tightly thus further inhibiting flow in an opposite direction.

FIG. 1 is a perspective view drawing of the top and side of a bidirectional, side-slit duckbill valve apparatus 100 configured for use with a guidewire (not shown in FIG. 1), according to an embodiment.

In an embodiment, a bidirectional side-slit duckbill valve apparatus 100 can comprise a flat washer section 101 located near a top end 102. This washer section 101 can be used to secure or seat the bidirectional side-slit duckbill valve apparatus 100 into a hub/cap (not shown in FIG. 1) or a similar device comprising a catheter apparatus, which can be configured to secure the bidirectional side-slit duckbill valve apparatus 100 into a particular position within the hub/cap, while also preventing fluids from flowing between the flat washer section 101 and a hub/cap in which it has been installed. The flat washer section 101 can comprise a first main opening 103 configured to allow fluids (not shown in FIG. 1) to flow through the opening 103. The diameter of the present bidirectional side-slit duckbill valve apparatus 100 can be 0.25 cm to 0.50 cm in an embodiment, but can also be configured to be much smaller or much larger in order to meet the requirements of typical bidirectional valves.

In an embodiment, the present apparatus 100 can comprise one or more side-slit valves 105 located near the second ends of each side section 209 and 219. These side-slit valves 105 can be configured to open when a negative pressure applied to the duckbill valve apparatus 100 through the first main opening 103. This negative pressure can be applied by a syringe or similar device if the catheter apparatus is used to draw blood from the patient. In an embodiment, both the duckbill valve opening 104 and the side-slit valves 105 can remain in a closed position when the duckbill valve apparatus 100 is subjected to a substantially neutral pressure.

In an embodiment, when a negative pressure is applied from the top end 102, through the first main opening 103 of the present duckbill valve apparatus 100, the second end 242 of the first side section 209 and the second end 241 of the second side section 219 comprising the duckbill valve can be pulled toward one another, which can simultaneously pull open the side-slit valves 105, which can be located adjacent to these second ends 241 and 242 and connected to these second ends 241 and 242, thus allowing fluids to flow through the side-slit valves 105. In an embodiment, the entire duckbill valve apparatus 100 can be comprised of a single piece of silicone, natural rubber, or a similar pliable material.

Figure 2A:
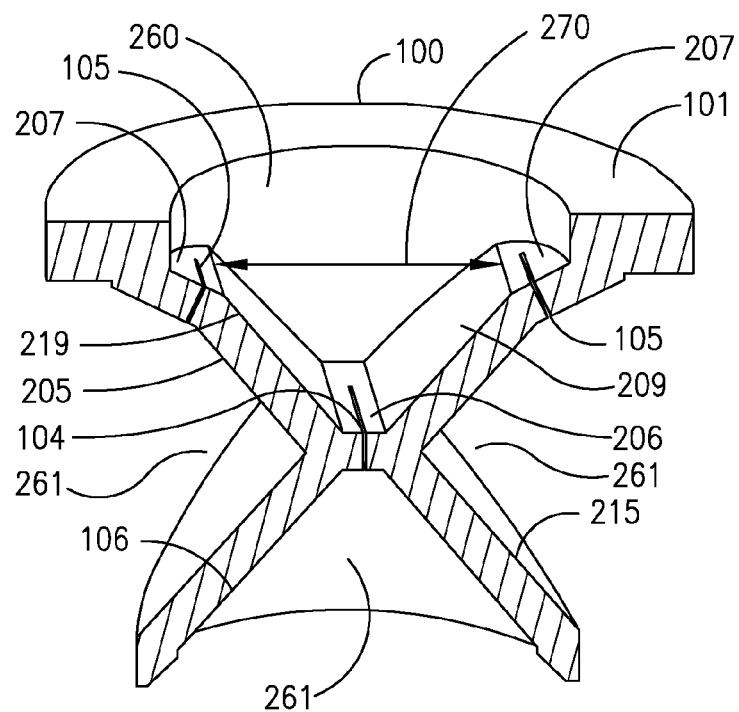
FIG. 2A is a cross-sectional perspective view drawing of the top and side of a bidirectional side-slit duckbill valve apparatus, shown in a neutral position, which is configured for use with a guidewire (not shown in FIG. 2A), wherein both the duckbill valve opening and the side-slit valves are in closed positions, according to an embodiment.

FIG. 2A is a cross-sectional perspective view drawing of the top and side of a bidirectional side-slit duckbill valve apparatus 100 configured for use with a guidewire (not shown in FIG. 2A), shown in a neutral position, wherein both the duckbill valve opening 104 and the side-slit valves 105 are in closed positions, according to an embodiment. In an embodiment, the first side section 209 can comprise a first end 232 and a second end 242 and the second side section 219 can comprise a first end 231 and a second end 241.

In FIG. 2A, the relative proximity of a duckbill valve opening 104 and two side-slit valves 105 is clearly shown, according to an embodiment. The duckbill valve opening 104 can be located in a trough 206 of the V-shaped upper section 205, comprised of the first side section 209 and the second side section 219, and the two side-slits 105 can be located on shoulders 207.

A funnel 106 for directing a guidewire, such as those that are commonly used to insert and properly install catheters within a patient's body, can be viewed in this figure. In an embodiment, fluid can flow through the duckbill valve opening 104 and through the funnel 106. A guidewire can be passed through, and directed by the funnel 106 and then pass through the duckbill valve opening 104. In this embodiment, fluid must be allowed to pass around the outer edges 256 of the funnel 106 in order to pass through one or more of the side-slit valves 105.

In an embodiment, the bidirectional side-slit duckbill valve apparatus 100 can comprise a V-shaped upper section 205 and an inverted V-shaped lower section 215, which also comprises the funnel 106 for directing a guidewire (not shown in FIG. 2A). The V-shaped upper section 205 can connect to the inverted V-shaped lower section 215 to form a shape that roughly forms an X-shape or hourglass shape. In an embodiment, the V-shaped upper section 205 can comprise the duckbill valve opening 104 and the two side-slit valves 105.

When the pressure differential between the top side 260 of the V-shaped upper section 205 and the bottom side 261 of the V-shaped lower section 215 is substantially zero, both the side-slit valves 105 and the duckbill valve opening 104 can remain in closed positions as shown in FIG. 2A. No fluid can flow through either the side-slit valves 105 or the duckbill valve opening 104 when each is in a closed position. The distance 270 between the second end 242 of the first side section 209 and the second end 241 of the second side section 219 can be at a maximum, and the side-slit valves 105 can be in closed positions when the pressure differential between the top side 260 of the V-shaped shaped upper section 205 and the bottom side 261 of the V-shaped lower section 215 is substantially zero, according to an embodiment.

Figure 2B:
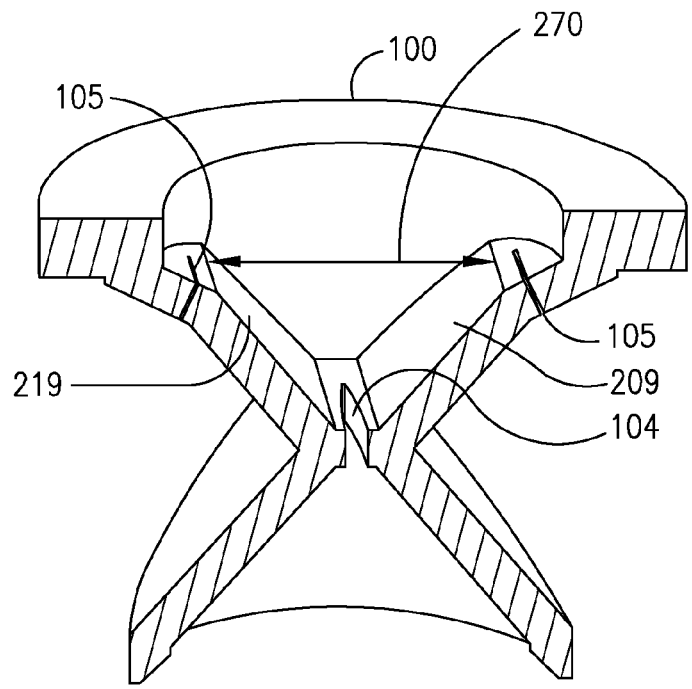
FIG. 2B is a cross-sectional perspective view drawing of the top and side of a bidirectional side-slit duckbill valve apparatus, shown in an injection position, which is configured for use with a guidewire (not shown in FIG. 2B), wherein two side-slit valves are in closed positions and the duckbill valve is in an open position, according to an embodiment.

FIG. 2B is a cross-sectional, top and side perspective view drawing of a bidirectional side-slit duckbill valve apparatus 100 configured for use with a guidewire (not shown in FIG. 2B), shown in an injection position, wherein two side-slit valves 105 are each in closed positions and the duckbill valve opening 104 is in an open position, according to an embodiment. FIG. 2B also shows flow in a first direction 290, which is from an area between the side sections 209 and 219 and through the duckbill valve opening 104.

In FIG. 2B, the duckbill valve opening 104 is in an open position, which can be caused by positive pressure being exerted against the first side section 209 and an the second side section 219. The side-slit valves 105 remain in a closed position because the distance 270 between the second end 242 of the first side section 209 and the second end 241 of the second side section 219 remains the same as the distance 270 shown in FIG. 2A (neutral position).

Figure 2C:
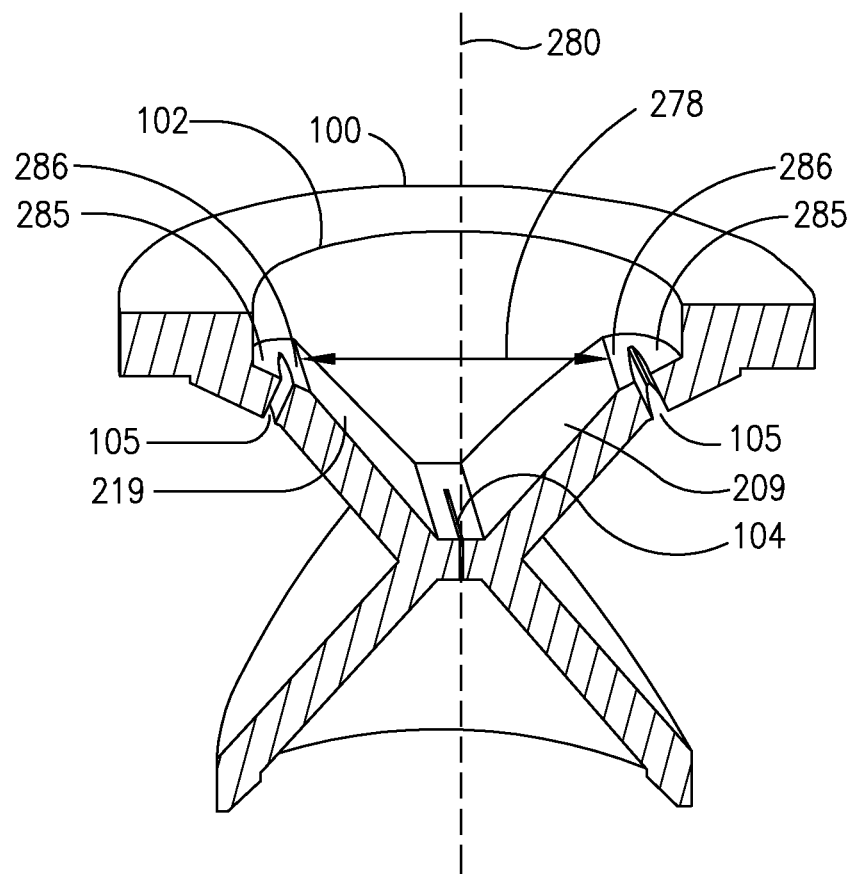
FIG. 2C is a cross-sectional perspective view drawing of the top and side of a bidirectional side-slit duckbill valve apparatus, shown in an aspiration position, which is configured for use with a guidewire (not shown in FIG. 2C), wherein the duckbill valve is in a closed position and the two side-slit valves are each in an open position, according to an embodiment.

FIG. 2C is a cross-sectional, top and side perspective view drawing of a bidirectional side-slit duckbill valve apparatus 100 configured for use with a guidewire (not shown in FIG. 2C), shown in an aspiration position, wherein the duckbill valve opening 104 is in a closed position and the two side-slit valves 105 are each in open positions, according to an embodiment. FIG. 2C also shows flow in a second direction 291, in the opposite direction from the first direction 290. In FIG. 2C the second direction can be from the inverted V-shaped lower section 215 through the side-slits 105 in an embodiment.

In FIG. 2C, the distance 278, between the second end 242 of the first side section 209 and the second end 241 of the second side section 219, is shorter than the distance 270 shown in FIGS. 2A and 2B due to movement of the first side section 209 and the second side section 219 inward toward a central axis 280 caused by negative pressure exerted from the top end 102 of the duckbill valve apparatus 100. This inward movement can pull the side-slit valves 105 open because an outer part 285 of the shoulder remains stationary due to its connection to the flat washer section 101, which also remains stationary, while the inner part 286 of the shoulder 207 is pulled toward the center axis 280 by the inward movement of the side sections 209 and 219.

Figure 2D:
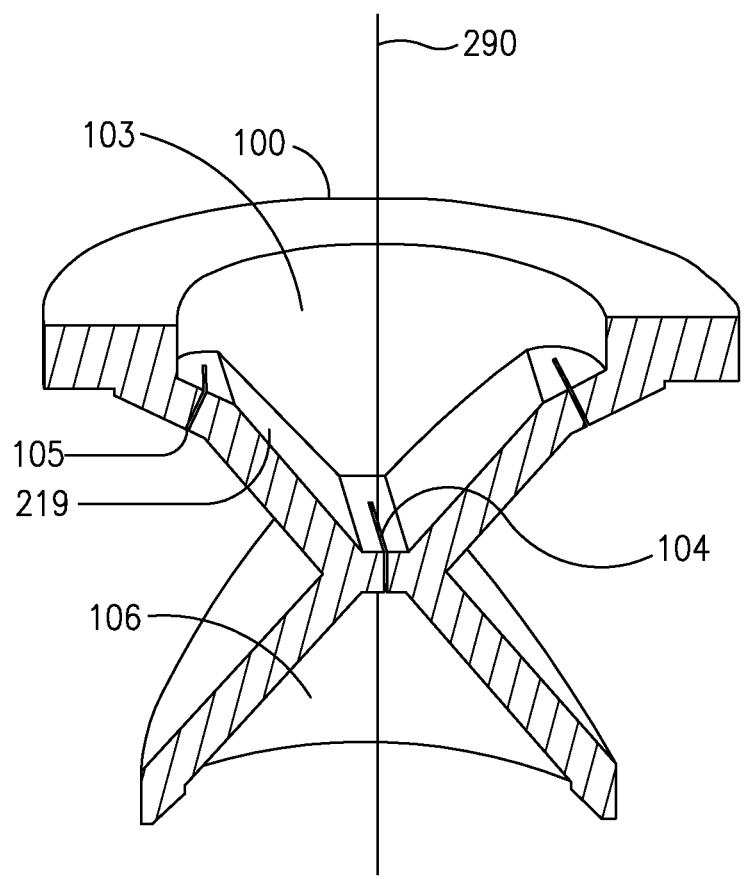
FIG. 2D is a cross-sectional perspective view drawing of the top and side of a bidirectional side-slit duckbill valve apparatus, shown in a neutral position, which is configured for use with a guidewire, wherein a guidewire has been guided through a funnel and through the duckbill valve opening, according to an embodiment.

FIG. 2D is a cross-sectional, top and side perspective view drawing of a bidirectional side-slit duckbill valve apparatus 100 configured for use with a guidewire 290, shown in a neutral position, wherein a guidewire 290 has been guided through a funnel 106 and through the duckbill valve opening 104, according to an embodiment.

In an embodiment, the funnel 106 can be used to direct the guidewire 290 through the inverted V-shaped lower section 215 and through the duckbill valve opening 104. Although the duckbill valve opening 104 can remain in a substantially closed position when the bidirectional side-slit duckbill valve apparatus 100 is in a neutral position, such as shown in FIG. 2D, the valve can be pliable enough to allow the guidewire 290 to be pushed through the duckbill valve opening 104, when it is in the closed position and then through the first opening 103 so that the guidewire can pass through the entire bidirectional side-slit duckbill valve apparatus 100. The guidewire 290 is for installation purposes, and therefore, is removed after the bidirectional side-slit duckbill valve apparatus 100 has been installed and before it is used.

Figure 3A:
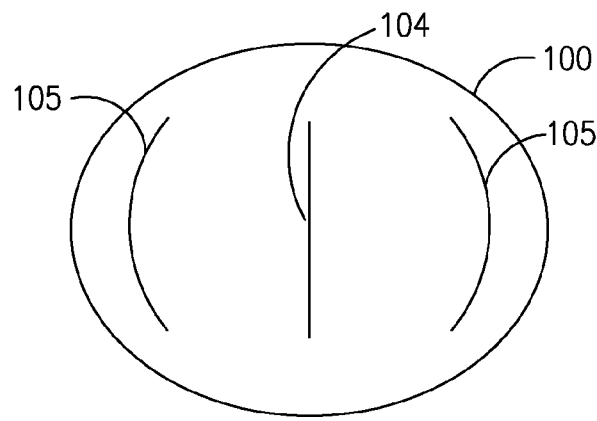
FIG. 3A is a top representational view drawing of the bidirectional side-slit duckbill valve apparatus in a neutral position, according to an embodiment.

FIG. 3A is a top representational view drawing of the bidirectional side-slit duckbill valve apparatus 100 in a neutral position, according to an embodiment.

In an embodiment, the duckbill valve opening 104 and the side-slit valves 105 can each be in closed positions when the bidirectional side-slit duckbill valve apparatus 100 is subjected to neither a substantially positive pressure nor a substantially negative pressure. In this way, the bidirectional side-slit duckbill valve apparatus 100 can be sealed when it is under neutral pressure and will not allow fluid to pass through it in either direction. In other words, no fluid is allowed to flow either through the duckbill valve opening 104 or through either of the side-slit valves 105 when the pressure differential on either side of these valves 104 and 105 is substantially zero.

Figure 3B:
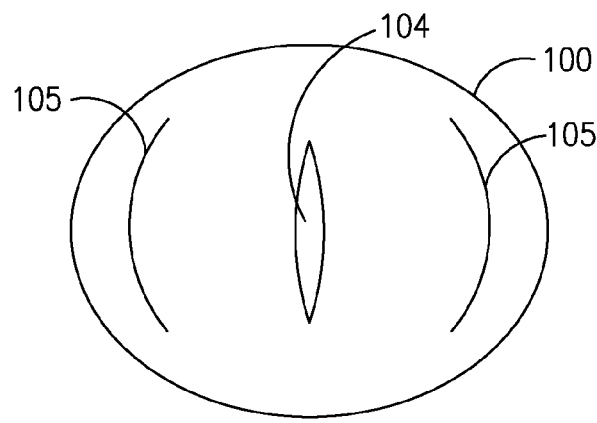
FIG. 3B is a top representational view drawing of the bidirectional side-slit duckbill valve apparatus in an injection position, according to an embodiment.

FIG. 3B is a top representational view drawing of the bidirectional side-slit duckbill valve apparatus 100 in an injection position, according to an embodiment. Injection is considered to be pressurized fluid flowing in a first direction from the top end 102 through the duckbill valve opening 104 as these parts are shown in FIGS. 1 thru 2D.

In an embodiment, the duckbill valve opening 104 can be in an open position and the side-slit valves 105 can each be in closed positions when fluid located above the duckbill valve opening 104 is subjected to a substantially positive pressure (pressure directed into the duckbill valve opening 104 from the top end 102). In this way, a fluid can be injected through the duckbill valve opening 104 in a first direction of the bidirectional side-slit duckbill valve apparatus 100 and this fluid can be allowed to first pass through the first opening 103 from the top end 102 through the valve opening 104 and out through the funnel 106 (from top to bottom using the orientation shown in FIG. 2). The positive pressure can originate from a liquid stream that has itself been subjected to a positive pressure (in this first direction), or positive pressure can originate from a manual injection of liquid into the top end 102 of the apparatus from a syringe or similar device.

Figure 3C:
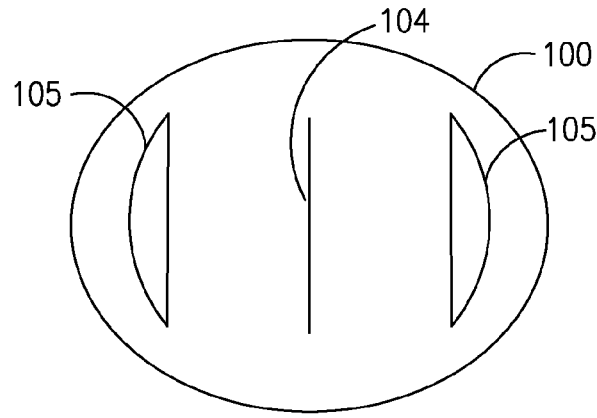
FIG. 3C is a top representational view drawing of the bidirectional side-slit duckbill valve apparatus in an aspiration position, according to an embodiment.

FIG. 3C is a top representational view drawing of the bidirectional side-slit duckbill valve apparatus 100, shown in an aspiration position, according to an embodiment. In the aspiration position liquid can flow in a second direction, opposite the first direction, out from the top end 102 (from bottom to top using the orientation in FIG. 2) when subjected to a negative pressure. Negative pressure can originate from a manual suction applied to the top end 102 that can pull liquid from areas located below the bottom side 261 (see FIG. 2A) of the V-shaped upper section 205 into areas above the top side 260 (see FIG. 2A) of the V-shaped upper section 205 through the side-slit valves 105, according to an embodiment. In this way, a fluid can be aspirated through the side-slit valves 105 comprising the bidirectional side-slit duckbill valve apparatus 100.

Figure 4:
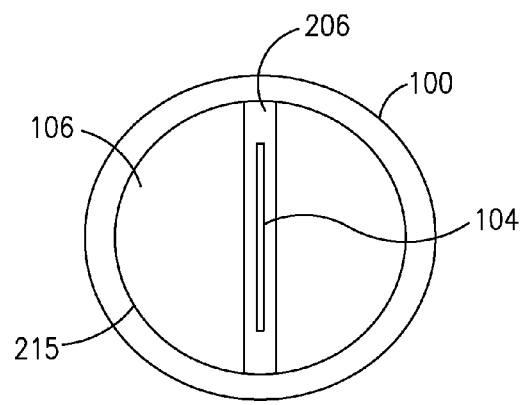
FIG. 4 is a bottom view drawing of a bidirectional side-slit duckbill valve apparatus configured for use with a guidewire (not shown in FIG. 4), according to an embodiment.

FIG. 4 is a bottom view drawing of a bidirectional side-slit duckbill valve apparatus 100 configured for use with a guidewire (not shown in FIG. 4), according to an embodiment.

In an embodiment, the duckbill valve opening 104 and trough 206 can be visible from the bottom, however, the side-slit valves 105 (not visible) may not be visible from the bottom because the a view of the side-slit valves 105 can be obscured by the funnel 106 comprising the inverted V-shaped lower section 215.

Figure 5:
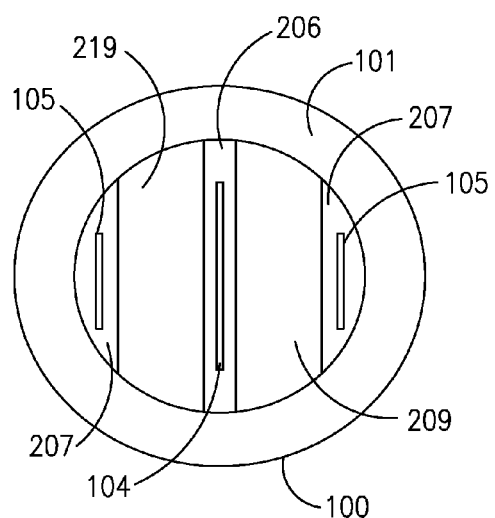
FIG. 5 is a top view drawing of a bidirectional side-slit duckbill valve apparatus configured for use with a guidewire (not shown in FIG. 5), according to an embodiment.

FIG. 5 is a top view drawing of a bidirectional side-slit duckbill valve apparatus 100 configured for use with a guidewire (not shown in FIG. 5), according to an embodiment.

This view clearly depicts the flat washer section 101, the shoulders 207 comprising the side-slit valves 105, the first side section 209 and the second side section 219 comprising the V-shaped upper section 205, and the trough 206 comprising the duckbill valve opening 104 in a particular embodiment. Each side-slit valve 105 can be connected to either side section 209 or side section 219 through a shoulder 207, which can be connected to the flat washer section 101.

In an embodiment, the shoulders 207 and the side sections 209 and 219 can be made from a single piece of pliable material, such as silicone, so that each side-slit valve 105 can be opened or closed by movement of the adjacent side section 209 or 219, which can pull upon or push upon the shoulders 207 when subjected to a substantially negative or positive pressure respectively. Thus, when positive pressure is applied to the bidirectional side-slit duckbill valve apparatus 100 in a first direction, the side sections 209 and 219 can be pushed in a direction perpendicular to the positive pressure and away from the duckbill valve opening 104 thereby further sealing the side-slit valves 105 while opening the duckbill valve opening 104. When negative pressure is applied to the bidirectional side-slit duckbill valve apparatus 100 in a second direction, this pressure causes the side sections 209 and 219 to contract inward, thereby further sealing the duckbill valve opening 104 while simultaneously opening the side-slit valves 105. The material comprising the side sections (and in one embodiment the entire apparatus) can be made from a malleable silicone, or similar malleable material that can bend and flex to a small degree when pressure is applied to it, thus enabling the movements described above. The positive and negative pressure can be applied via a positively or negatively pressurized liquid or a positively or negatively pressurized gas. For example, a hypodermic needle, when used to extract blood from a patient, would first generate a suction pressure immediately before the blood starts to flow out of the patient. This suction pressure constitutes a negative pressure which would cause the contractions and valve movements described above thereby allowing the blood to flow only in the second direction.

Figure 6:
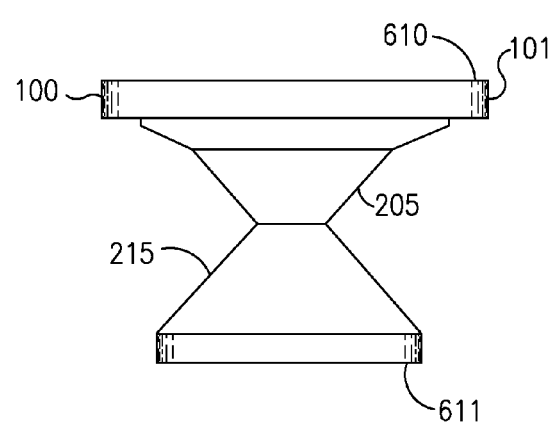
FIG. 6 is a side view drawing of a bidirectional side-slit duckbill valve apparatus configured for use with a guidewire (not shown in FIG. 6), according to an embodiment.

FIG. 6 is a side view drawing of a bidirectional side-slit duckbill valve apparatus 100 configured for use with a guidewire (not shown in FIG. 6), according to an embodiment.

In this view, the X-shape or hourglass shape of this embodiment is clearly visible as formed by the V-shaped upper section 205 and an inverted V-shaped lower section 215. This view also shows the relative size and location of the flat washer section 101 in relation to the upper and lower sections 205 and 215. This figure also illustrates the relative top 610 and bottom 611 of the bidirectional side-slit duckbill valve apparatus 100, according to an embodiment.

Figure 7:
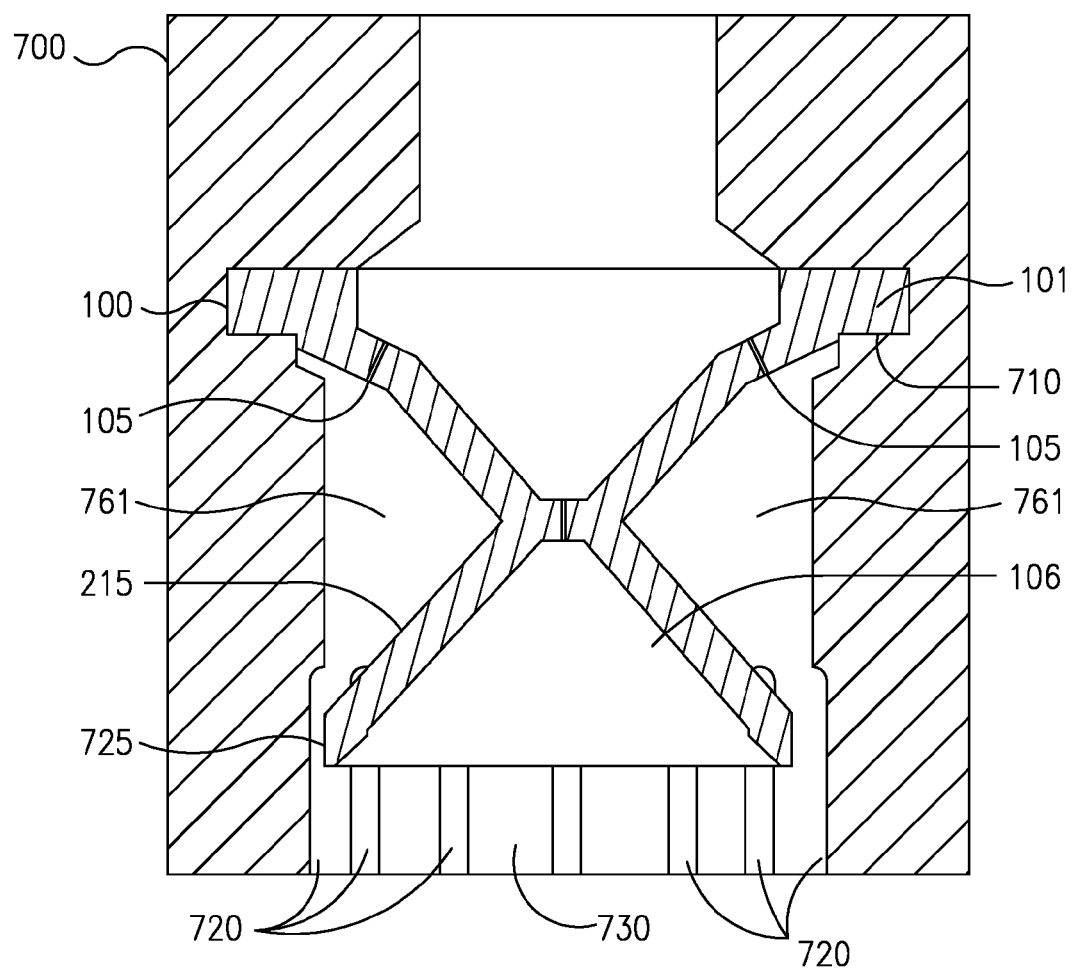
FIG. 7 is a cross-sectional, side view drawing of a bidirectional side-slit duckbill valve apparatus configured for use with a guidewire (not shown in FIG. 7), seated within a modified hub/cap, according to an embodiment.

FIG. 7 is a cross-sectional, side view drawing of a bidirectional side-slit duckbill valve apparatus 100 configured for use with a guidewire (not shown in FIG. 7), housed within a modified hub/cap 700, according to an embodiment. The hub/cap can have a top opening 740 and a bottom opening 741. The top opening 740 can allow liquid to flow into the bidirectional side-slit duckbill valve apparatus 100 in a first direction, as shown in FIG. 2B, and the bottom opening 741 can allow liquid to flow into the bidirectional side-slit duckbill valve apparatus 100 in a second direction, shown in FIG. 2C, opposite the first direction.

In an embodiment the bidirectional side-slit duckbill valve apparatus 100 can be secured in place by a modified hub/cap 700 configured to secure the bidirectional side-slit duckbill valve apparatus 100. This modified hub/cap 700 can comprise a washer groove 710 configured to receive the flat washer section 101, which can be used to secure the flat washer section 101, and by extension, the entire bidirectional side-slit duckbill valve apparatus 100 to the modified hub/cap 700. In an embodiment, the flat washer section 101 can be placed into the washer groove 710 by pressing it into position through a bottom opening 730 in the modified hub/cap 700, which can be facilitated by the flexibility of the bidirectional side-slit duckbill valve apparatus 100 as it can be comprised of silicone or a similar pliable material.

In an alternative embodiment (not shown in FIG. 7), the modified hub/cap 700 can be comprised of two sections, connected either along a horizontal axis or a vertical axis that can allow the modified hub/cap 700 to be split into two sections allowing access to an inner section 765 of the modified hub/cap 700. The bidirectional side-slit duckbill valve apparatus 100 could then be placed within the modified hub/cap 700 and the two sides of the modified hub/cap 700 could be connected back together.

In an embodiment, the inverted V-shaped lower section 215 can be suspended within the modified hub/cap 700 and the modified hub/cap 700 can comprise one or more channels 720 or similar features located near where a bottom 725 of the inverted V-shaped lower section 215 of the bidirectional side-slit duckbill valve apparatus 100. These channels 720 can provide one or more paths for fluid to flow around the bottom 725 of the inverted V-shaped lower section 215 when the fluid is aspirated through the slide-slit valves 105.

The embodiment shown in FIG. 7 can allow for the use of a funnel 106 to direct a guidewire through the bidirectional side-slit duckbill valve apparatus 100 while also allowing aspirated fluid to flow through the bottom opening 741 around the bottom 725 of the inverted V-shaped lower section 215, comprising the funnel 106, through the channels 720, to reach the slide-slit valves 105 and pass through the bidirectional side-slit duckbill valve apparatus 100 from bottom to top as its orientation is shown in FIG. 7. To ensure proper threading of the guidewire into the funnel 106, the bottom 725 of the inverted V-shaped lower section 215 can be configured to conform closely to the bottom opening 730 of the modified hub/cap 700 and the channels 720 can have a diameter that is smaller than that of a standard guidewire, in an embodiment.

Each of these measures can be utilized in order to help prevent a guidewire from bypassing the funnel 106 and accessing areas 761 below the side-slit valves 105. However, these measures can still allow fluid to flow around the bottom 725 of the inverted V-shaped lower section 215 sufficiently so that no flow voids can exist in the areas 761 located below the side-slit valves 105. Flow voids are areas of stagnant flow where blood or other fluids can be allowed to clot or otherwise coagulate and clog the bidirectional side-slit duckbill valve apparatus 100 when mounted in the modified hub/cap 700.

Figure 8:
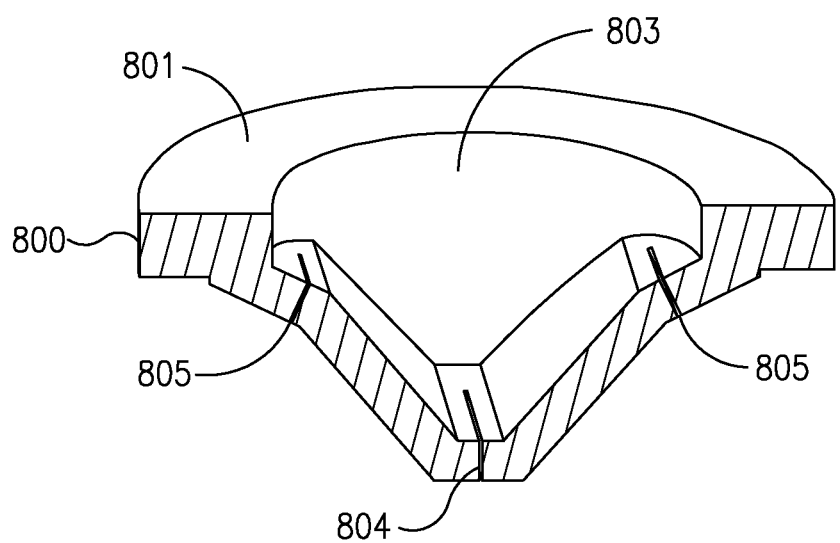
FIG. 8 is a cross-sectional, top and side perspective view drawing of a bidirectional side-slit duckbill valve apparatus, which is not configured for use with a guidewire, according to an embodiment.

FIG. 8 is a top and side cross-sectional perspective view drawing of a bidirectional side-slit duckbill valve apparatus 800, which is not configured for use with a guidewire, according to an embodiment.

In this embodiment, the bidirectional side-slit duckbill valve apparatus 800 can essentially consist only of the V-shaped upper section, very similar to the V-shaped upper section 215 shown in FIGS. 1 thru 7 of the bidirectional side-slit duckbill valve apparatus 100. No funnel 106, such as that shown in FIGS. 2 and 7 above, is required if a guidewire will not be used in connection with the bidirectional side-slit duckbill valve apparatus 800. Therefore, the inverted V-shaped lower section 215, as shown in FIGS. 1, 2, 6 and 7 above, comprising the funnel 106, will also not be necessary. Likewise, the bidirectional side-slit duckbill valve apparatus 800 would not require a modified hub/cap 700 comprising one or more channels 720, as shown in FIG. 7 above, to facilitate the flow of aspirated fluid around the funnel 106, as shown in FIGS. 1, 2, 6 and 7 above, and through the side-slit valves 805.

In all other respects, the bidirectional side-slit duckbill valve apparatus 800 embodiment can perform identically to the bidirectional side-slit duckbill valve apparatus 100 embodiment shown in FIGS. 1 thru 7. Specifically, fluid can be injected through a duckbill valve opening 804 in a first direction when a substantially positive pressure is applied to the fluid through a first opening 803 in a flat washer section 801 (from top to bottom in the orientation shown in FIG. 8). Fluid can also be aspirated in a second direction, opposite the first direction, through side-slit valves 805 when a substantially negative pressure is applied through the first opening 803 causing fluid to flow from bottom to top in the orientation shown in FIG. 8.

Figure 9:
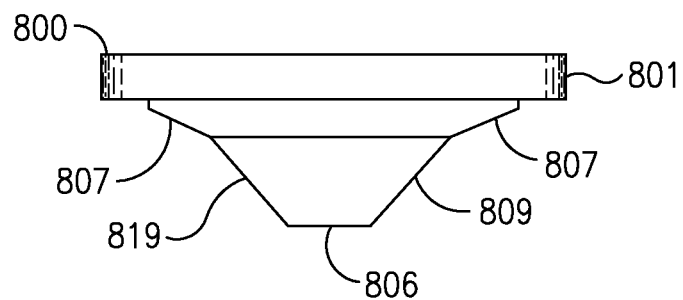
FIG. 9 is a side view drawing of a bidirectional side-slit duckbill valve apparatus, which is not configured for use with a guidewire, according to an embodiment.

FIG. 9 is a side, perspective view drawing of a bidirectional side-slit duckbill valve apparatus 800, which is not configured for use with a guidewire, according to an embodiment.

This view shows the relative positions of the flat washer section 801, shoulders 807, first side section 809, second side section 819 and a trough 806 to each other.

Figure 10:
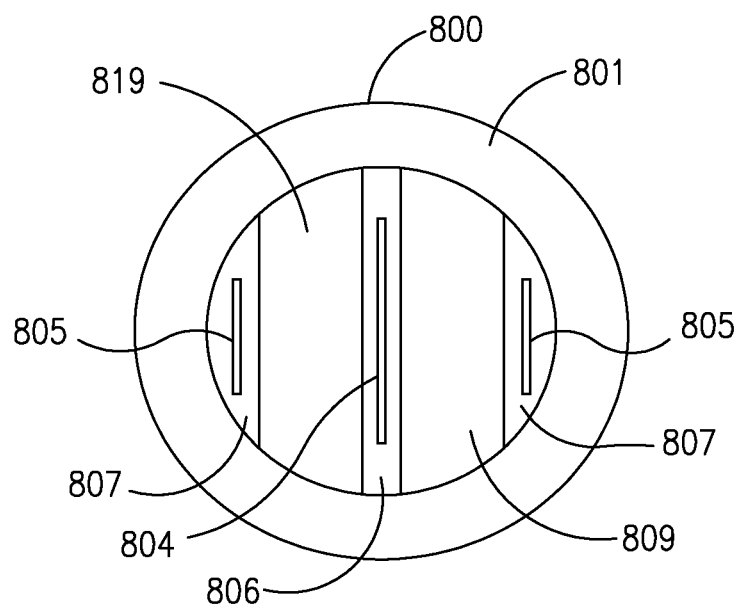
FIG. 10 is a top view drawing of a bidirectional side-slit duckbill valve apparatus, which is not configured for use with a guidewire, according to an embodiment.

FIG. 10 is a top view drawing of a bidirectional side-slit duckbill valve apparatus 800, which is not configured for use with a guidewire, according to an embodiment.

The bidirectional side-slit duckbill valve apparatus 800 can comprise a flat washer section 801, shoulders 807 comprising the side-slit valves 805, a first side section 809 and the second side section 819 and a trough 806 comprising the duckbill valve opening 804.

Figure 11:
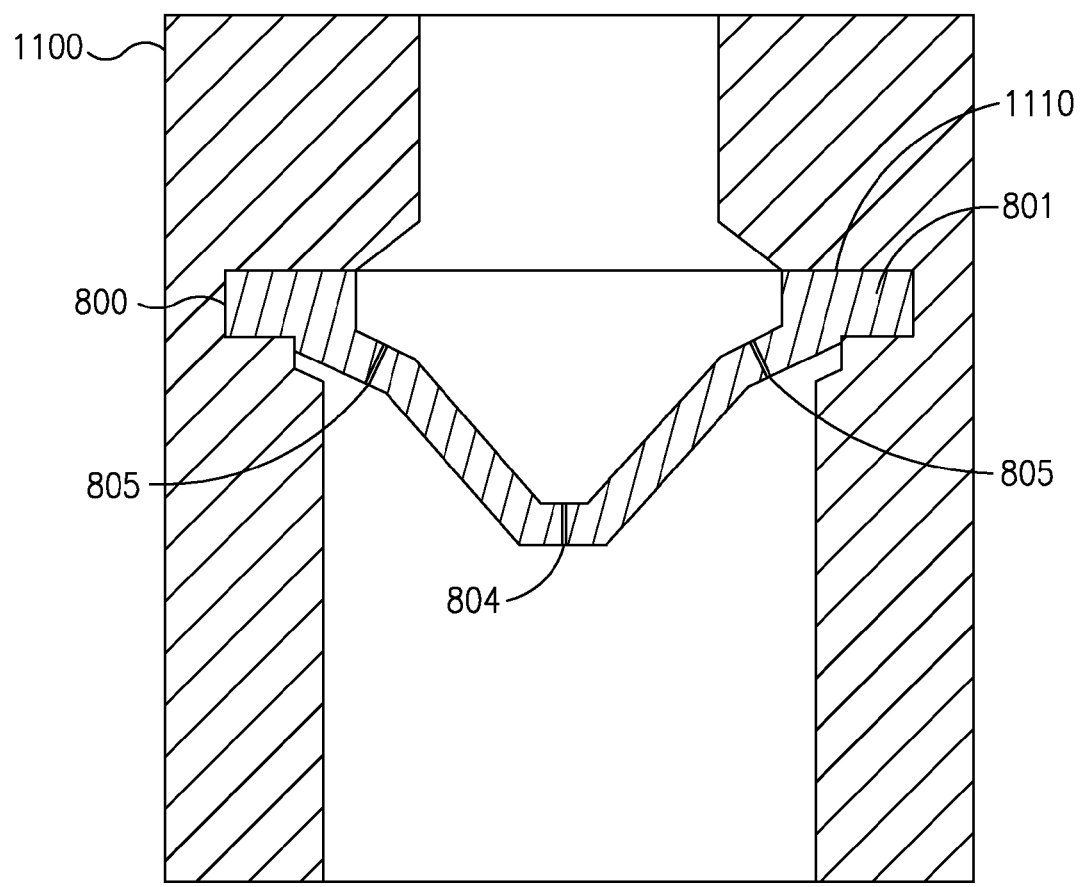
FIG. 11 is a cross-sectional, side perspective view drawing of a bidirectional side-slit duckbill valve apparatus, which is not configured for use with a guidewire, seated within a hub/cap, according to an embodiment.

FIG. 11 is a cross-sectional, side perspective view drawing of a bidirectional side-slit duckbill valve apparatus 800, which is not configured for use with a guidewire, shown seated in a hub/cap 1100, according to an embodiment. The hub/cap can have a top opening 1140 and a bottom opening 1141. The top opening 1140 can allow liquid to flow into the bidirectional side-slit duckbill valve apparatus 800 in a first direction, as shown in FIG. 2B, and the bottom opening 1141 can allow liquid to flow into the bidirectional side-slit duckbill valve apparatus 800 in a second direction, shown in FIG. 2C, opposite the first direction.

As discussed above, the elimination of a funnel and inverted V-shaped lower section 215 means that the hub/cap 1100 would no longer require channels 720 (shown in FIG. 7) or similar passages for aspirated fluid to flow around an inverted V-shaped lower section 215 (as shown in FIGS. 1 thru 7) to reach the side-slit valves 805 in order to flow through the bidirectional side-slit duckbill valve apparatus 800. In an embodiment, the hub/cap 1100 can contain empty space 1165 below the bidirectional side-slit duckbill valve apparatus 800. Therefore, the hub/cap 1100 shown in FIG. 11 can comprise a washer groove 1110 configured to accept the flat washer section 801, but would not require passages such as the channels 720 shown in FIG. 7.

All parts herein can be made of the standard materials used for such objects known in the art. For example, the two embodiments of bidirectional side-slit duckbill valve apparatuses, 100 and 800, can be comprised of silicone in an embodiment. The two embodiments of the hubs/caps, 700 and 1100 can be comprised completely or in part, from plastic, glass, or any other suitable material.

The many features and advantages of the present device are apparent from the detailed specification, and thus it is intended by the appended claims to cover all such features and advantages of the present device that fall within the true spirit and scope of the inventive concept. Further, since numerous modifications and changes will readily occur to those skilled in the art, it is not desired to limit the present inventive concept to the exact construction and operation illustrated and described, and accordingly all suitable modifications and equivalents may be resorted to, falling within the scope of the present inventive concept.

What is claimed is:

1. A bidirectional side-slit duckbill valve apparatus, comprising:
V-shaped upper section comprising a first side section having a first end and a second end and a second side section having a first end and a second end, wherein the first side section is connected to a first shoulder at its first end and a trough at its second end and the second side section is connected to a second shoulder at its first end and the trough at its second end;
the trough comprises a duckbill valve opening; and
the first shoulder comprises a first side-slit valve and the second shoulder comprises a second side-slit valve.

2. The apparatus as recited in claim 1 wherein a first direction is from an area between the side sections through the duckbill valve opening, and a second direction is a direction opposite the first direction;
wherein the duckbill valve opening is configured to allow fluid pressurized in the first direction to flow through it and prevent fluid pressurized in the second direction to flow through it;
wherein the first side-slit valve and the second side-slit valve are both configured to allow fluid pressurized in the second direction to flow through them and prevent fluid pressurized in the first direction to flow through them; and wherein the duckbill valve opening, the first side-slit valve and the second side-slit valve are all configured to not allow fluid that is not pressurized to flow through them in either the first direction or the second direction.

3. The apparatus as recited in claim 1, further comprising a flat washer section connected to both the first shoulder and the second shoulder.

4. The apparatus as recited in claim 1, further comprising an inverted V-shaped lower section connected to the trough.

5. The apparatus as recited in claim 4, wherein the inverted V-shaped lower section comprises a funnel configured to direct a guidewire through the duckbill valve opening.

6. The apparatus as recited in claim 1, wherein the bidirectional side-slit duckbill valve apparatus is comprised of silicone.

7. The apparatus as recited in claim 4 wherein a first direction is from an area between the side sections through the duckbill valve opening, and a second direction is a direction opposite the first direction;

wherein the duckbill valve opening is configured to allow fluid pressurized in the first direction to flow through it and prevent fluid pressurized in the second direction to flow through it;

wherein the first side-slit valve and the second side-slit valve are both configured to allow fluid pressurized in the second direction to flow through them and prevent fluid pressurized in the first direction to flow through them; and wherein the duckbill valve opening, the first side-slit valve and the second side-slit valve are all configured to not allow fluid that is not pressurized to flow through them in either the first direction or the second direction.

8. The apparatus as recited in claim 4, further comprising a flat washer section connected to both the first shoulder and the second shoulder.

9. The apparatus as recited in claim 4, wherein the bidirectional side-slit duckbill valve apparatus is comprised of silicone.

10. A bidirectional side-slit duckbill valve and hub/cap apparatus, comprising:

a V-shaped upper section, comprising a first side section having a first end and a second end and a second side section having a first end and a second end, wherein the first side section is connected to a first shoulder at its first end and a trough at its second end and the second side section is connected to a second shoulder at its first end and a trough at its second end;

the trough comprises a duckbill valve opening;

the first shoulder comprises a first side-slit valve and the second shoulder comprises a second side-slit valve;

a flat washer section connected to both the first shoulder and the second shoulder;

an inverted V-shaped lower section, comprising a funnel configured to direct a guidewire through the duckbill valve opening; and a hub/cap configured to securely hold the flat washer section placed within a flat washer section groove, the hub/cap having a top opening and a bottom opening.

11. The apparatus as recited in claim 10, wherein the hub/cap comprises one or more channels near the bottom opening.

12. A bidirectional side-slit duckbill valve and hub/cap apparatus, comprising:

a V-shaped upper section, comprising a first side section having a first end and a second end and a second side section having a first end and a second end, wherein the first side section is connected to a first shoulder at its first end and a trough at its second end and the second side section is connected to a second shoulder at its first end and a trough at its second end;

the trough comprises a duckbill valve opening;

the first shoulder comprises a first side-slit valve and the second shoulder comprises a second side-slit valve;

a flat washer section connected to both the first shoulder and the second shoulder; and a hub/cap configured to securely hold the flat washer section placed within a flat washer section groove, the hub/cap having a top opening and a bottom opening.

13. The apparatus as recited in claim 12, wherein the hub/cap is comprised of plastic.

14. A method for using a bidirectional side-slit duckbill valve apparatus; the method comprising:

providing a V-shaped upper section, comprising a first side section having a first end and a second end and a second side section having a first end and a second end, wherein the first side section is connected to a first shoulder at its first end and a trough at its second end and the second side section is connected to a second shoulder at its first end and a trough at its second end;

the trough comprises a duckbill valve opening; and the first shoulder comprises a first side-slit valve and the second shoulder comprises a second side-slit valve; and an inverted V-shaped lower section, comprising a funnel configured to direct a guidewire through the duckbill valve opening;

wherein a first direction is from an area between the side sections through the duckbill valve opening, and a second direction is a direction opposite the first direction;

wherein the duckbill valve opening is configured to allow fluid pressurized in the first direction to flow through it and prevent fluid pressurized in the second direction to flow through it;

wherein the first side-slit valve and the second side-slit valve are both configured to allow fluid pressurized in the second direction to flow through them and prevent fluid pressurized in the first direction to flow through them; and wherein the duckbill valve opening, the first side-slit valve and the second side-slit valve are all configured to not allow fluid that is not pressurized to flow through them in either the first direction or the second direction;

providing a fluid pressurized in the first direction; and providing a fluid pressurized in the second direction;

injecting the fluid pressurized in the first direction through the duckbill valve opening; and aspirating the fluid pressurized in the second direction through at least one side-slit valve.

15. A method for using a bidirectional side-slit duckbill valve and hub/cap apparatus; the method comprising:

providing a V-shaped upper section, comprising a first side section having a first end and a second end and a second side section having a first end and a second end, wherein the first side section is connected to a first shoulder at its first end and a trough at its second end and the second side section is connected to a second shoulder at its first end and a trough at its second end;

the trough comprises a duckbill valve opening; and the first shoulder comprises a first side-slit valve and the second shoulder comprises a second side-slit valve; and an inverted V-shaped lower section, comprising a funnel configured to direct a guidewire through the duckbill valve opening;

a hub/cap configured to securely hold the flat washer section placed within a flat washer section groove, the hub/cap having a top opening and a bottom opening;

wherein a first direction is from an area between the side sections through the duckbill valve opening, and a second direction is a direction opposite the first direction;

wherein the duckbill valve opening is configured to allow fluid pressurized in the first direction to flow through it and prevent fluid pressurized in the second direction to flow through it;

wherein the first side-slit valve and the second side-slit valve are both configured to allow fluid pressurized in the second direction to flow through them and prevent fluid pressurized in the first direction to flow through them; and wherein the duckbill valve opening, the first side-slit valve and the second side-slit valve are all configured to not allow fluid that is not pressurized to flow through them in either the first direction or the second direction;

providing a fluid pressurized in the first direction; and providing a fluid pressurized in the second direction;

injecting the fluid pressurized in the first direction through the first opening of the hub/cap and through the duckbill valve opening; and aspirating the fluid pressurized in the second direction through the second opening of the hub/cap and through at least one side-slit valve.

\* \* \* \* \*